United States Patent [19]

Butterworth et al.

[11] Patent Number: 5,345,946
[45] Date of Patent: Sep. 13, 1994

[54] MULTI-ELEMENT SURGICAL DRAPE WITH SEALABLE SURGICAL RUN-OFF POUCHES

[75] Inventors: David Butterworth, Colleyville; Susan L. O'Connell, Arlington, both of Tex.

[73] Assignee: Johnson & Johnson Medical, Inc., Arlington, Tex.

[21] Appl. No.: 52,257

[22] Filed: Apr. 23, 1993

[51] Int. Cl.⁵ .................. A61B 19/08; A61B 19/00
[52] U.S. Cl. ...................... 128/853; 128/849
[58] Field of Search .................. 128/849–857

[56] References Cited

U.S. PATENT DOCUMENTS

| | | | |
|---|---|---|---|
| 4,024,862 | 5/1977 | Collins | 128/854 |
| 4,186,786 | 2/1980 | Kirkpatrick | 383/63 |
| 4,316,455 | 2/1982 | Stoneback | 128/853 |
| 4,316,456 | 2/1982 | Stoneback | 128/853 |
| 4,476,860 | 10/1984 | Collin et al. | 128/852 |
| 4,869,271 | 9/1989 | Idris | 128/849 |
| 4,938,698 | 7/1990 | Chantry | 434/253 |
| 5,010,899 | 4/1991 | Thompson | 128/849 |
| 5,038,798 | 8/1991 | Dowdy et al. | 128/849 |
| 5,074,316 | 12/1991 | Dowdy | 128/849 |
| 5,143,091 | 9/1992 | Patnode et al. | 128/849 |
| 5,161,544 | 2/1992 | Morris | 128/849 |
| 5,222,507 | 6/1993 | Taylor | 128/849 |

Primary Examiner—Robert A. Hafer
Assistant Examiner—Michael O'Neill
Attorney, Agent, or Firm—James Riesenfeld

[57] ABSTRACT

A multi-element surgical drape includes a bottom sheet that is placed over a patient and a top sheet that is reversibly secured to the bottom sheet. The two sheets each have a fenestration, and the fenestrations are aligned to provide access to the surgical site. After the surgical procedure has been completed the two sheets are separated. The top sheet is contaminated ("red-bag") medical waste, while the bottom sheet can be disposed of as non-contaminated waste, recycled, or processed for reuse. The invention permits a substantial reduction in the volume of red-bag waste generated by surgery.

7 Claims, 10 Drawing Sheets

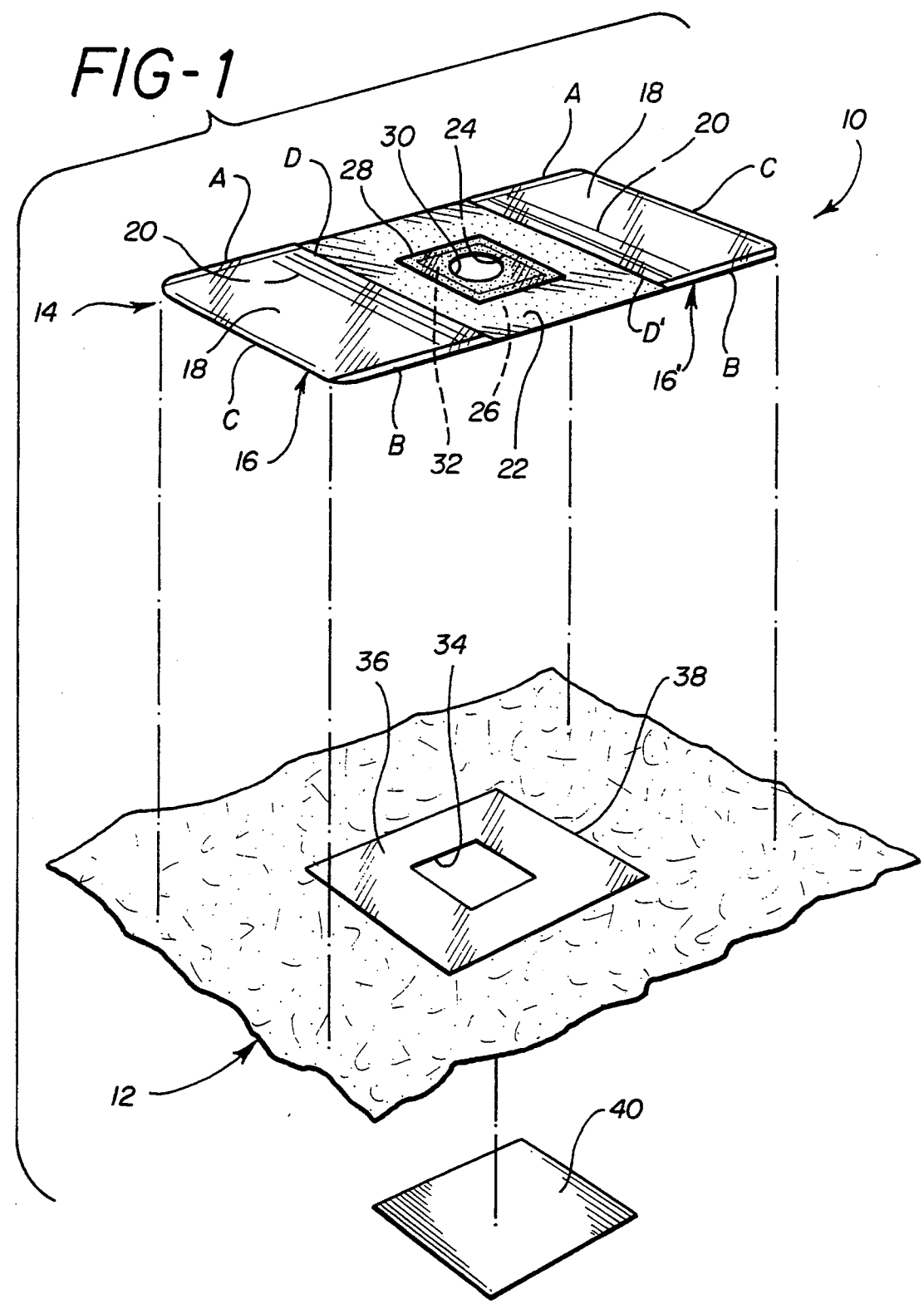

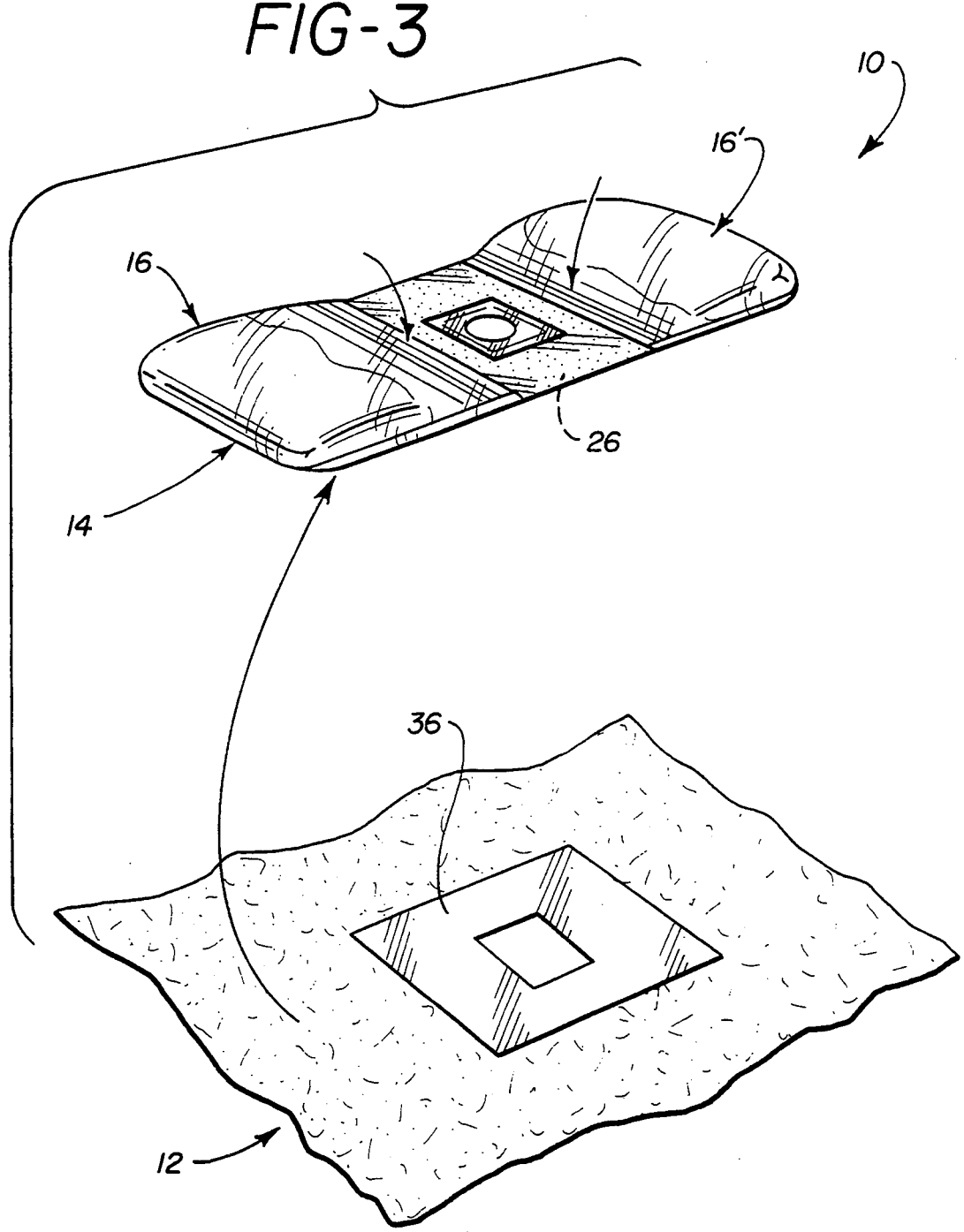

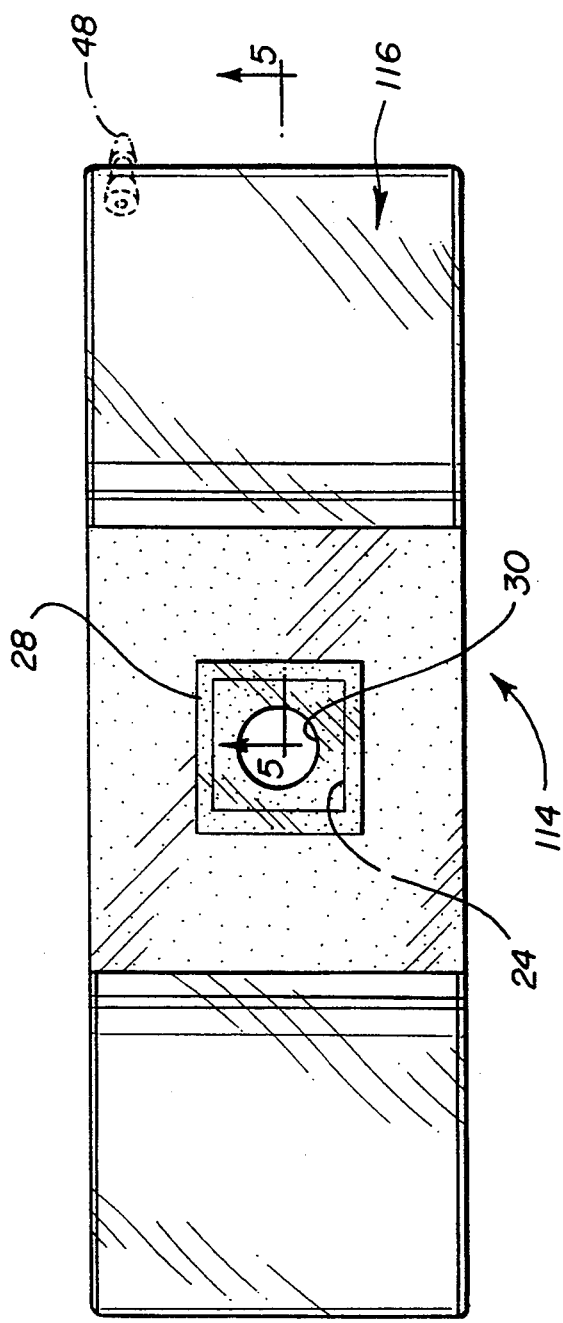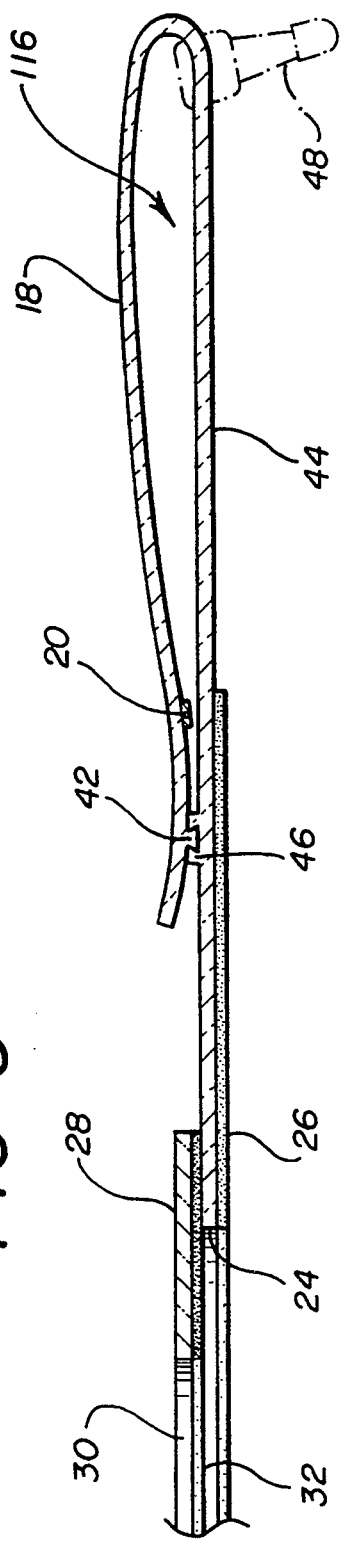

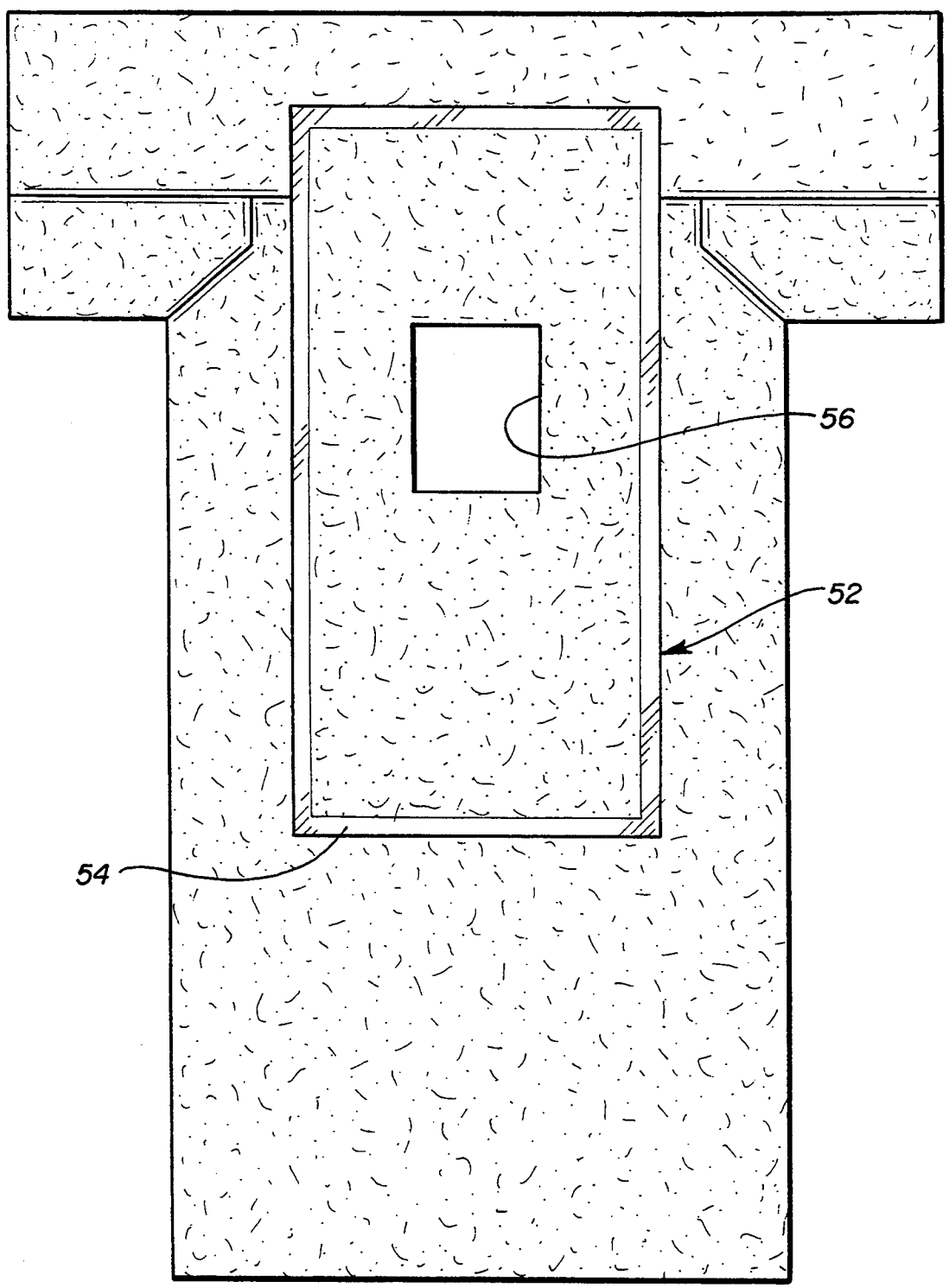

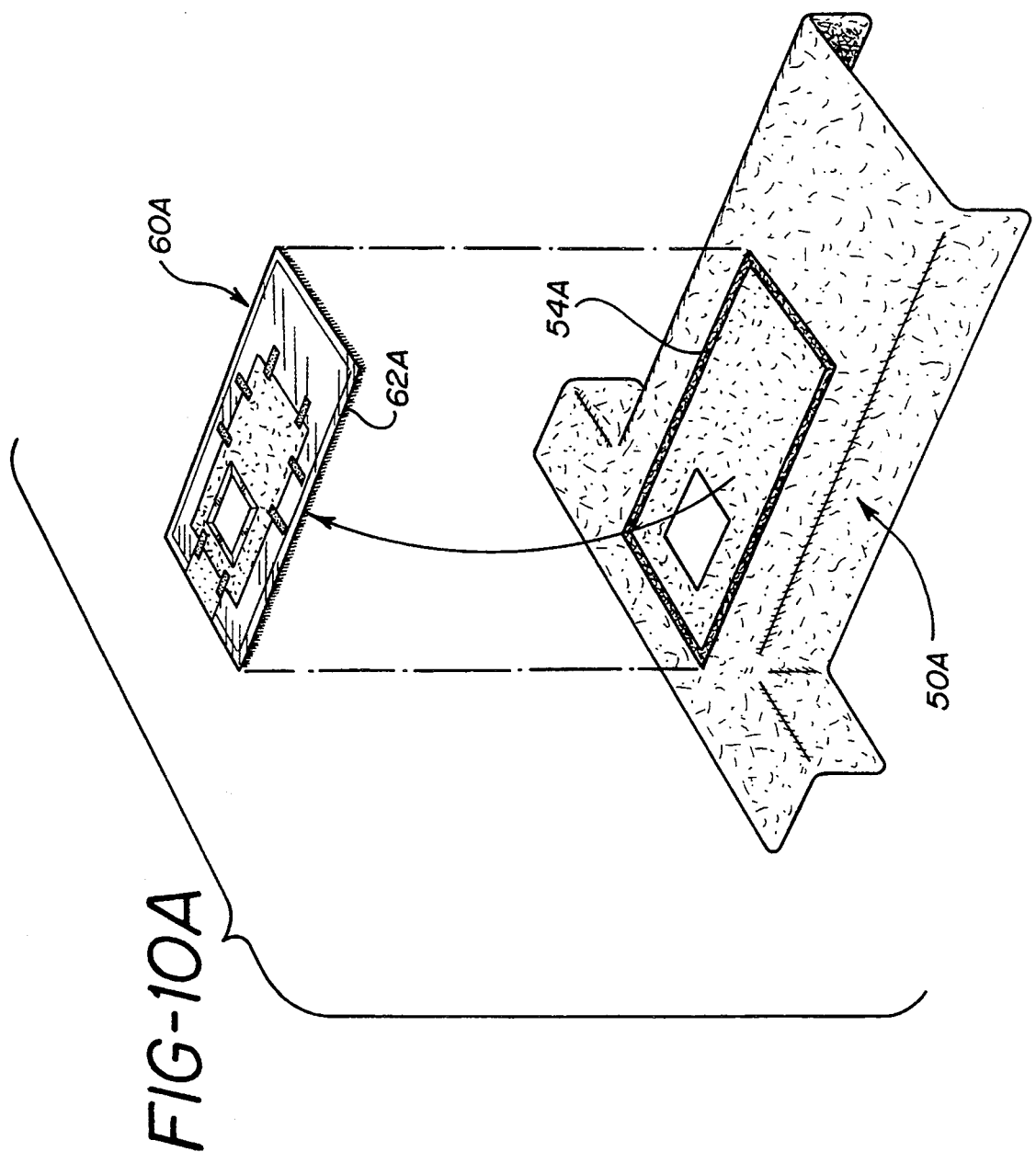

MULTI-ELEMENT SURGICAL DRAPE WITH SEALABLE SURGICAL RUN-OFF POUCHES

BACKGROUND OF THE INVENTION

1. Field of the Invention

This invention relates to surgical drapes; more particularly, to multi-element drapes that can be separated after use into contaminated and non-contaminated elements.

2. Description of the Related Art

Surgical drapes are used to maintain a sterile field in the vicinity of a surgical site, in order to prevent infection or contamination. In the process of use, a surgical drape becomes contaminated with blood and other body fluids. The contaminated drapes must be carefully segregated, so that they do not spread pathogens into the environment. Used disposable drapes must be "red-bagged;" i.e., maintained separately from non-contaminated waste. With the increasing concern regarding the potential environmental and waste disposal problems posed by contaminated medical waste, disposing of red-bag waste in an acceptable manner is becoming increasingly expensive. There is thus an incentive to reduce the amount of contaminated waste generated by surgical procedures (See, e.g., Tieszen ME and Gruenberg JC, "A Quantitative, Qualitative, and Critical Assessment of Surgical Waste," JAMA 267, 2765 [May 27, 1992]).

A number of patents disclose inventions that relate to the present invention. U.S. Pat. No. 4,024,862, issued on May 24, 1977, to R.F. Colins, discloses a drape that includes auxiliary elements. Specifically, a conventional surgical drape includes a fenestration that is large enough to perform an enlarged surgical procedure, but the fenestration is covered by one or more "frame sheets" removably secured to the upper surface of the drape around the fenestration. The frame sheet has a smaller fenestration aligned with the large fenestration in the drape. Thus a reduced surgical procedure may be performed through the fenestration of the frame sheet or, alternatively, the frame sheet can be removed in order to perform the enlarged procedure.

U.S. Pat. Nos., 4,316,455 and 4,316,456, issued on Feb. 23, 1982, to W.K. Stoneback, disclose a draping system designed to reduce the inventory that a hospital must stock. The system makes use first of a small drape that is placed in contact with the patient and that includes a fenestration for placement over the operative site. Thereafter, a large "standardized" top sheet is placed over the bottom drape. The larger top drape, which has a fenestration that is larger than that of the bottom drape but smaller than the outer periphery of the bottom drape, is positioned so that the fenestrations are aligned. The top drape is then secured to the bottom drape.

U.S. Pat. No. 4,476,860, issued on Oct. 16, 1984, to R.F. Collins, discloses a drape comprising a main sheet that has adhered to its top surface (away from the patient) a transparent sheet, which includes pockets for holding instruments and collecting body fluids, and a reinforcement sheet. A fenestration extends through the main sheet, transparent sheet, and reinforcement sheet.

U.S. Pat. No. 5,074,316, issued on Dec. 24, 1991, to R. C. Dowdy, discloses a drape for brachial angiography and an instrument pouch that may be secured removably to the drape near the surgical site.

Surgical drapes are known that include fluid-collection pouches near a fenestration for collecting fluids generated during the surgical procedure. Such drapes are available, for example, from Neuromedics, Inc., Sugar Land, Tex. and Alcon Surgical, Fort Worth, Tex. The pouches on these drapes have no provision for closing them after use to prevent leakage.

None of these patents suggest a multi-element drape that permits a separation of contaminated from non-contaminated elements after use. Nor do drapes of the prior art suggest such multi-element drapes.

SUMMARY OF THE INVENTION

In accordance with the present invention, a multi-element surgical drape comprises
a) a bottom sheet for placement over a patient and comprising
  i) a bottom surface for contacting the patient,
  ii) a top surface for facing away from the patient after placement,
  iii) attachment receptor means on the top surface, and
  iv) a fenestration;
b) a top sheet comprising
  i) a bottom surface facing the bottom sheet and a top surface facing away from the bottom sheet,
  ii) attachment means on the bottom surface that attach to the receptor means on the bottom sheet to removably secure the top sheet to the bottom sheet, and
  iii) a fenestration smaller than, and aligned with, the fenestration in the bottom sheet; and
c) a pouch on the top surface of the top sheet, near the fenestration, for collecting fluid runoff during surgery, the pouch comprising
  i) a top edge and bottom edge joined by two opposing side edges, the side edges and bottom edge being sealed closed, and
  ii) means for detachably sealing the top edge to permit opening the pouch to receive fluid and then closing the pouch to prevent leakage of the fluid.

The drape limits contamination to the top sheet and the fluid collection means, which can be removed after the procedure is completed. Thereafter, the bottom sheet can be disposed of as non-contaminated waste, recycled, or processed for reuse.

In another embodiment of the present invention, a multi-element surgical drape comprises
a) a bottom sheet for placement over a patient and comprising
  i) a bottom surface for contacting the patient,
  ii) a top surface for facing away from the patient after placement,
  iii) first attachment means on the top surface,
  iv) guide means to indicate a preselected position on the top surface, and
  v) a fenestration and
b) a top sheet for placement over the bottom sheet in the preselected position, comprising
  (i) a bottom surface for facing the bottom sheet and a top surface for facing away from the bottom sheet,
  (ii) second attachment means on the bottom surface that attaches to the first attachment means on the bottom sheet to removably secure the top sheet to the bottom sheet, and
  (iii) a fenestration smaller than the fenestration in the bottom sheet and aligned with the fenestration in the bottom sheet when the top sheet is in the preselected position.

This embodiment likewise limits contamination to the top sheet and also provides a modular system in which a standard bottom sheet can be used—and, if desired, reused—for any one of a variety of procedures, by securing to it a disposable top sheet designed for the particular procedure.

A method of draping and undraping a surgical patient in accordance with the present invention comprises (a) securing a top sheet to a bottom sheet, wherein
   (i) the bottom sheet comprises a fenestration and an attachment receptor means that surrounds the fenestration and
   (ii) the top sheet comprises
       (1) a bottom surface facing the bottom sheet and a top surface facing away from the bottom sheet.
       (2) attachment means on the bottom surface that attaches to the receptor means on the bottom sheet to accomplish the securing together of the sheets, and
       (3) a fenestration smaller than, and aligned with, the fenestration in the bottom sheet;
(b) separating and removing the top sheet from the bottom sheet after the patient has undergone a surgical procedure;
(c) removing the bottom sheet from the patient; and
(d) identifying the top sheet for disposal and the bottom sheet for reuse or recycling.

BRIEF DESCRIPTION OF THE DRAWINGS

FIG. 1 is an exploded perspective view of a surgical drape of the present invention.

FIG. 3 is a perspective view of the drape of FIG. 2 after the surgical procedure has been completed and the top and bottom sheets of the drape have been separated.

FIG. 4 is a top plan view of a top sheet of the present invention.

FIG. 5 is a cross section through the top sheet as taken along line 5—5 of FIG. 4.

FIG. 6 is a top plan view of a bottom sheet of the present invention.

FIG. 10A is a perspective view of another embodiment of a drape after surgery and after the top and bottom sheets have been separated.

DETAILED DESCRIPTION OF THE INVENTION

Figure 1A:
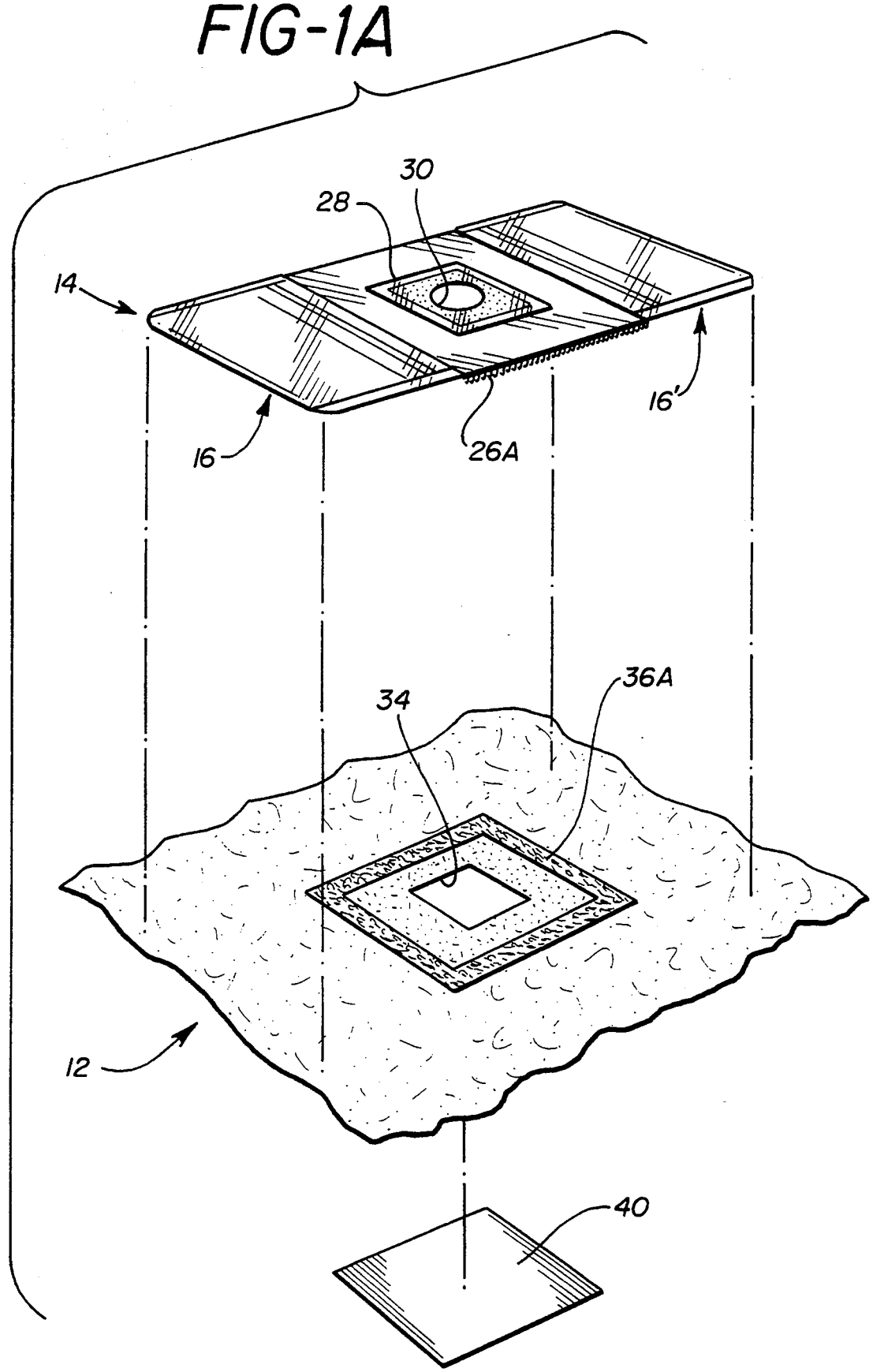
FIG. 1A is an exploded perspective view of another embodiment of a surgical drape of the present invention.

Surgical drapes isolate the operative site to maintain sterility and to prevent contamination. To serve that purpose, drapes typically cover not only most or all of the patient, but also cover the operating table, arm boards, walls of the anesthesia area, etc. Thus, surgical drapes involve many square feet of material and after they are used make a substantial contribution to the medical waste disposal problem.

There is rising concern regarding the potential health and environmental problems that are posed by medical waste and its disposal. Efforts to reduce the volume of medical waste are focused primarily on contaminated ("red bag") waste, for which strict standards have been developed for proper handling and disposal.

The present invention addresses this concern by providing a multi-element drape that can easily be separated after use into a red-bag element, whose segregation and disposal is relatively costly, and a "brown-bag" element that can be disposed of in a conventional landfill, recycled, or processed for reuse.

FIG. 1 is an exploded view of a drape of the present invention adapted for surgical procedures that generate large quantities of fluid, which may include blood, other body fluids, irrigation fluid, etc. The drape 10 includes a bottom sheet 12 and a top sheet 14. Opposite ends of sheet 14 may be folded upon themselves and side edges A and B sealed, by heat for example, to form pouches 16 and 16'. Alternatively, the pouches may be formed by placing sheets over each end of sheet 14 and sealing edges A, B, and C of the contiguous sheets. Alternatively, only a single pouch may be formed, and pouch elements are generally discussed above and below with respect to pouch 16 alone. The top panel 18 of pouch 16 has an optional bendable strip 20 near unsealed edge D. As shown in FIG. 2, the strip may be bent so as to maintain the pouch in the open position in order to collect fluids during the surgery.

Between the top edges D and D' of pouches 16 and 16', central area 22 of top sheet 14 has a fenestration 24 and a releasable and refastenable adhesive 26 coated on its bottom surface to adhere top sheet 14 to bottom sheet 12. Incise section 28 is adhered to top sheet 14 in the region surrounding fenestration 24 and has cut into it fenestration 30. Fenestration 30 may be cut during the manufacturing process or, alternatively, it may be cut by a healthcare worker in preparation for surgery. Fenestration 30 in incise section 28 is smaller than fenestration 24 in top sheet 14, and the underside of incise section 28 is coated with adhesive 32 to adhere to the patient's skin in the area surrounding the surgical site.

In principle, incise section 28 would not be needed, with fenestration 30 simply being cut into top sheet 14. However, since the role of adhesive 26 (to releasably adhere top sheet 14 to bottom sheet 12) is different from that of adhesive 32 (to securely adhere the drape to the patient in the region that surrounds the surgical site, without irritating the patient's skin), it is preferable to have an incise section 28.

Bottom sheet 12 has a fenestration 34 that is larger than, and aligned with, fenestration 30 in incise section 28. Adhesive 26 secures the top sheet 14 to optional receptor layer 36, which in turn is either permanently attached to bottom sheet 12 or is simply the top surface of bottom sheet 12. Optional guidelines 38 guide the proper positioning of central area 22 for joining top sheet 14 to bottom sheet 12. Release liner 40 covers the adhesive 32 that is on the underside of incise section 28. After removal of the release liner, the drape is placed on the patient, with fenestration 30 surrounding the surgical site and the adhesive 32 adhering the drape to the patient in the region that surrounds the surgical site.

Figure 2:
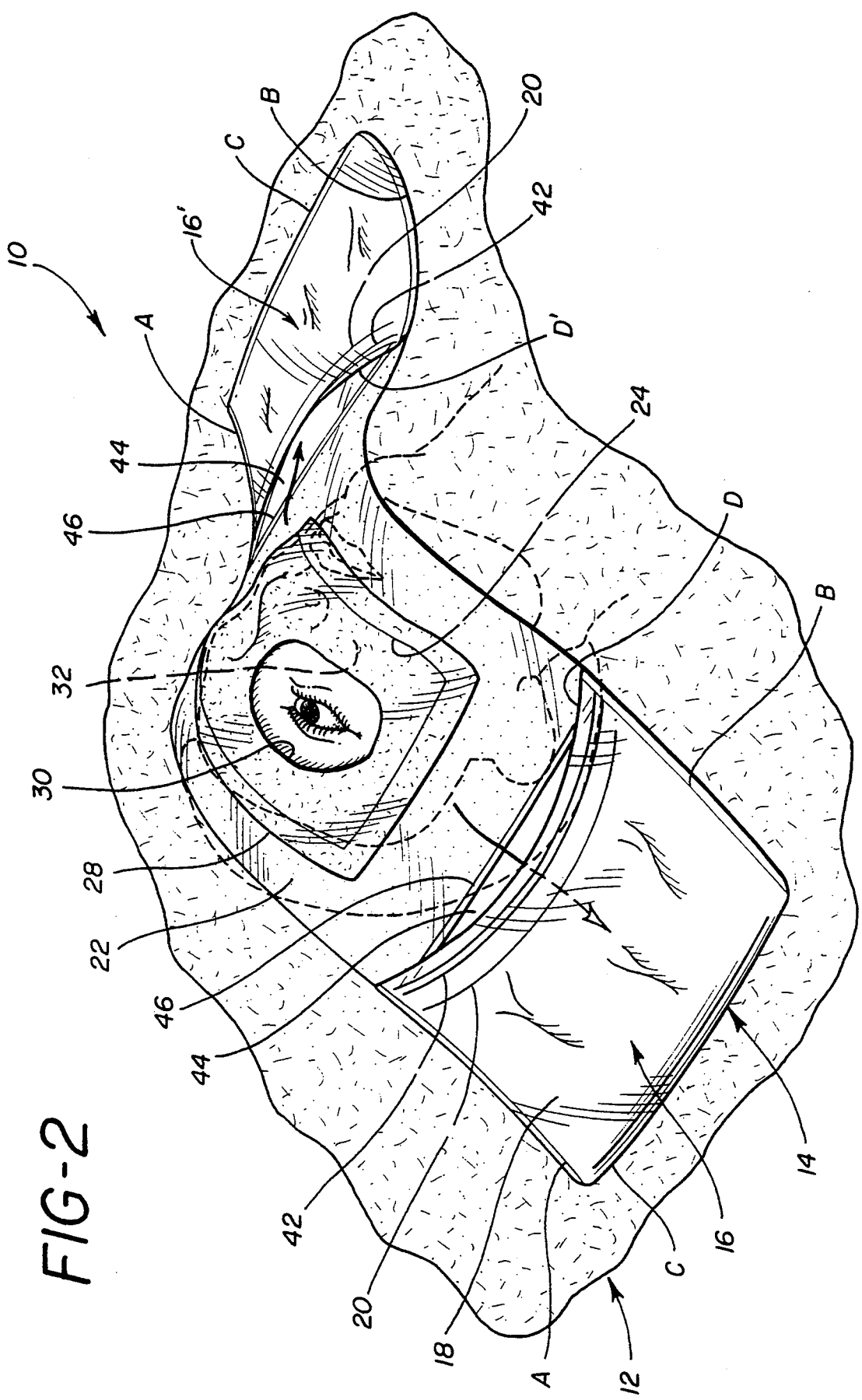
FIG. 2 is a perspective view of an ophthalmic drape of the present invention.

FIG. 1A depicts an exploded view of another embodiment of the drape of FIG. 1 in which an attachment layer 26A on the perimeter of sheet 14 and a corresponding receptor layer 36A on sheet 12 form a hook-and-loop (velcro) fastener system.

FIG. 2 is a perspective view of a drape 10 of this invention in place on a patient. Although the drape shown is an ophthalmic drape, it is clear that this type of drape, appropriately modified, can be used for a variety of procedures. Top panel 18 of pouch 16 has a raised ridge 42 that extends outward from its surface near, and parallel to, edge D. Bottom panel 44 of pouch 16 has a channel structure 46 positioned so that it can engage raised ridge 42, thereby sealing pouch 16 when top panel 18 is pushed against bottom panel 44. The sealing mechanism is depicted in cross section in FIG. 5, discussed below.

FIG. 3 is a perspective view, which shows that pouch 16 is sealed after the surgery is complete, and the pouch and top sheet 14 are removed from bottom sheet 12. The top sheet 14 and pouch 16 constitute contaminated, red-bag waste. Bottom sheet 12 is not contaminated and, depending on its material, can be brown-bagged for disposal in landfill, can be recycled, or can be laundered and sterilized for reuse. Any suitable disposable or reusable material may be used for sheet 12. If reusable, the material must maintain its body fluid and pathogen barrier properties throughout its lifecycle. A preferred material that can be recycled is a polyethylene nonwoven fabric.

FIG. 4 is a plan view of a top sheet 114 of a drape of this invention that includes a sealable drain port 48 to permit fluid to be drained from pouch 116.

FIG. 5 is a cross section through the sheet of FIG. 4.

The structure of a large variety of surgical drapes is such that there is considerable similarity among the parts of the drape that are distant from the surgical site. The differences among these drapes are largely found within a comparatively small area that surrounds the surgical site. Another embodiment of the present invention takes advantage of this fact by providing a "universal" bottom sheet, which is used in conjunction with one of a variety of top sheets. The top sheet is selected as appropriate for the particular procedure that is to be performed. It is attached to the bottom sheet in preparation for the surgery and removed from the bottom sheet for disposal after the surgery has been completed.

FIG. 6 depicts a universal bottom sheet 50 for a surgical drape of this invention. A region of sheet 50 has on its top surface a guide 52 to indicate a position on the surface. As depicted in FIG. 6, guide 52 consists of a pattern of release tape 54. Fenestration 56 provides access to a surgical site when the sheet is over a patient. Bottom sheet 50 may be of any suitable disposable or reusable drape material known in the art. Preferably, it comprises a recyclable material, such as a polyethylene nonwoven material.

Figure 7:
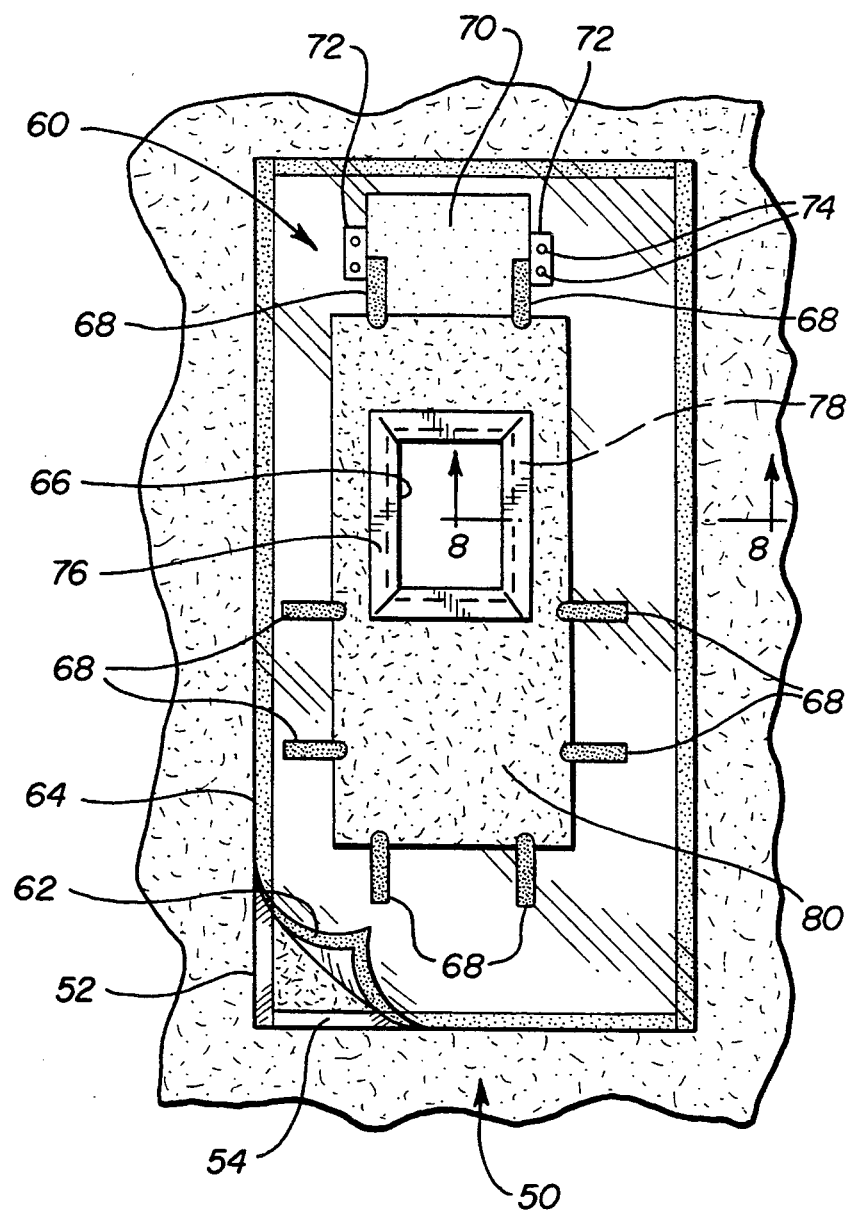
FIG. 7 is a top plan view of an endoscopic drape formed when a top sheet is secured to the bottom sheet of FIG. 6.

FIG. 7 depicts a top sheet 60 secured to the bottom sheet 50 of FIG. 6 to form a drape for endoscopic abdominal surgery. Preferably, an adhesive 62 rings the bottom surface of the peripheral area 64 of sheet 60, and the adhesive is covered with a release liner before the sheets are combined. Proper positioning is then accomplished by aligning peripheral area 64 of sheet 60 with guide 52 of sheet 50, removing the release liner from adhesive 62, and then releasably securing the peripheral area to release tape 54. A convenient form of releasable adhesive is a double-faced tape, where the opposite face is coated with a non-release (i.e., permanent) adhesive. Since the bottom sheet is to be reused or recycled, if the releasable adhesive 62 were on bottom sheet 50, it would have to survive repeated reprocessing (such as laundering and sterilization) or would have to be recyclable. Those requirements do not apply to the adhesive when, as shown, it is on top sheet 60. Thus, releasable adhesive 62 need not be, but preferably is, on the bottom surface of top sheet 60. Preferably, the sheet that doesn't have the adhesive has a release layer that contacts the adhesive layer and facilitates separation of the sheets. Releasable adhesives and release layers suitable for the practice of this invention are available from Medical Specialties Div. of 3M Health Care, St. Paul, Minn.

The periphery of fenestration 66 is entirely included within the periphery of fenestration 56. The elements of top sheet 50 are substantially the same as the elements that surround the fenestration of a conventional drape for endoscopic surgery, such as the Barrier * Laparoscopic Abdominal Sheet, available from Johnson & Johnson Medical, Inc. Arlington, Tex. These conventional elements include velcro fasteners 68 to secure cords and tubes to the sheet; instrument pad 70; and utility flaps 72, to which instruments may be clamped. Holes 74 in the utility flaps also hold cords and tubes. Surrounding fenestration 66 are a non-linting layer 76, which provides a backing for an adhesive 78 for adhering the sheet to the patient, and a bactericidal/reinforcement fabric 80.

Figure 8:
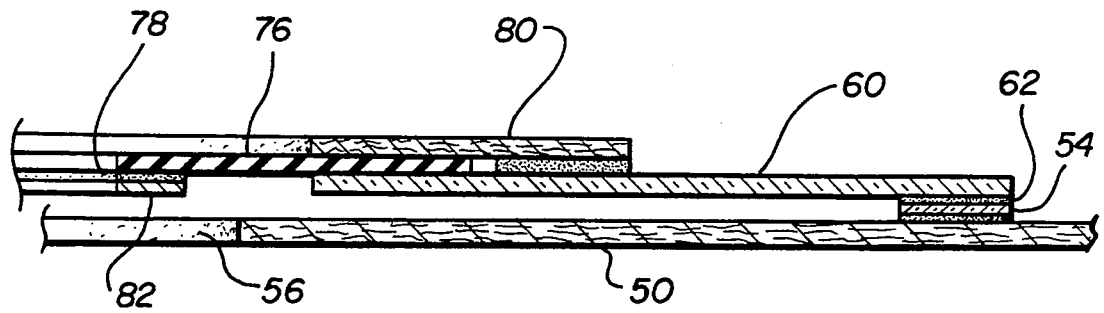
FIG. 8 is a cross section through the endoscopic drape as taken along line 8—8 of FIG. 7.

The structure of the elements that surround the fenestration can be better understood with reference to the cross section depicted in FIG. 8. Release liner 82 covers adhesive layer 78 coated on non-linting backing layer 76. Bactericidal fabric 80 provides reinforcement and enhances infection prevention.

Figure 9:
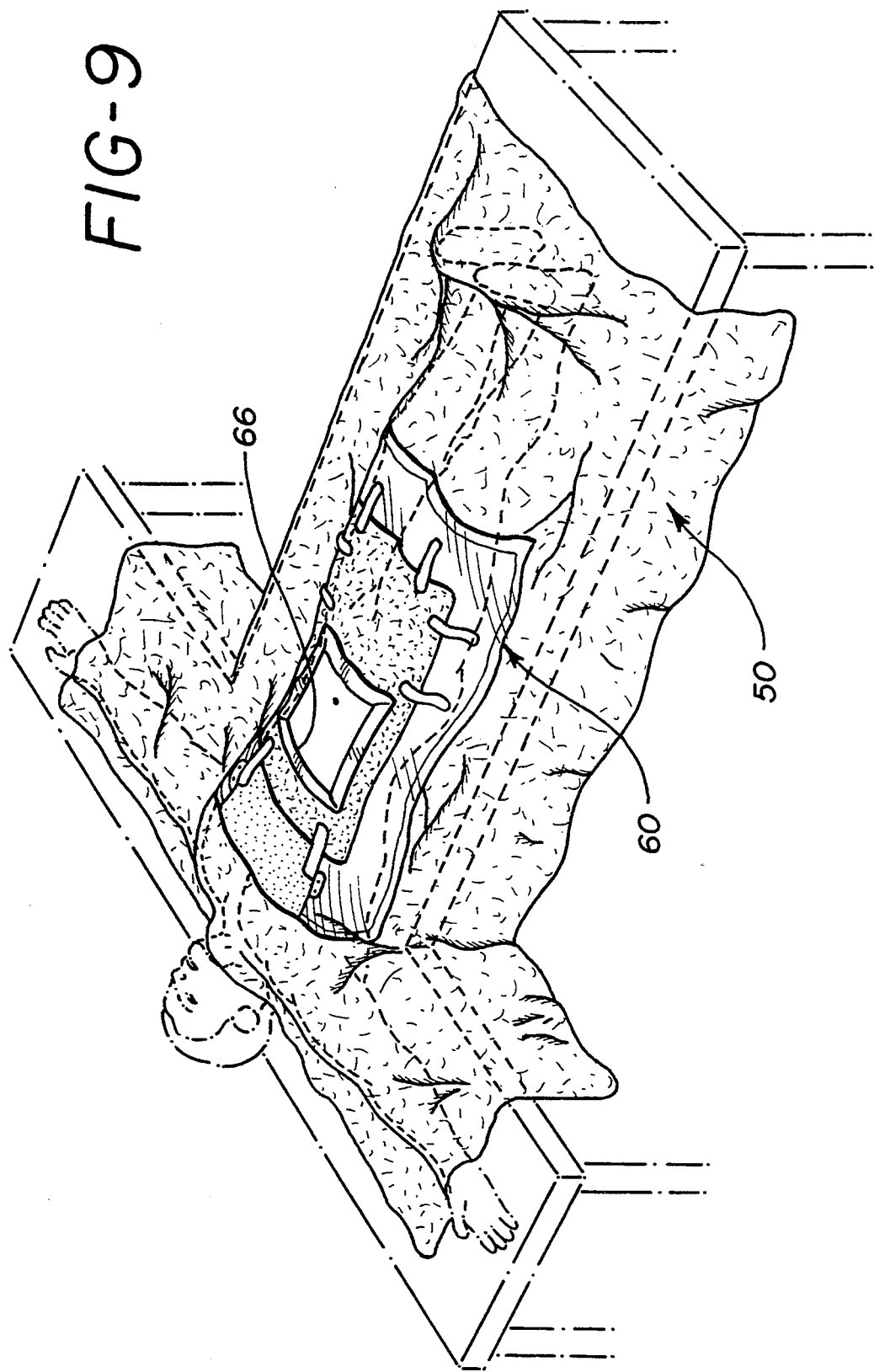
FIG. 9 is a perspective view of a laparoscopic abdominal drape of the present invention.

FIG. 9 depicts the endoscopic abdominal ("laparoscopic") drape of FIG. 7 in place on a surgical patient. Note that drapes for any one of a variety of surgical procedures may be formed by securing to a bottom sheet 50 a top sheet that has the appropriate fenestration and elements in the region surrounding the fenestration. In each case, the elements of the top sheet are substantially similar to those that would be in the region surrounding the fenestration of a conventional drape used for this same procedure. In addition to drapes for a variety of endoscopic procedures, drapes that can be replaced by a multi-element drape of this invention include caesarean section, extremity, hip, and pediatric. Details regarding conventional drapes for these procedures appear in product catalogs and product sheets available from Johnson & Johnson Medical, Inc., Arlington, Tex. many but not all cases, a single universal design of bottom sheet can be used.

Figure 10:
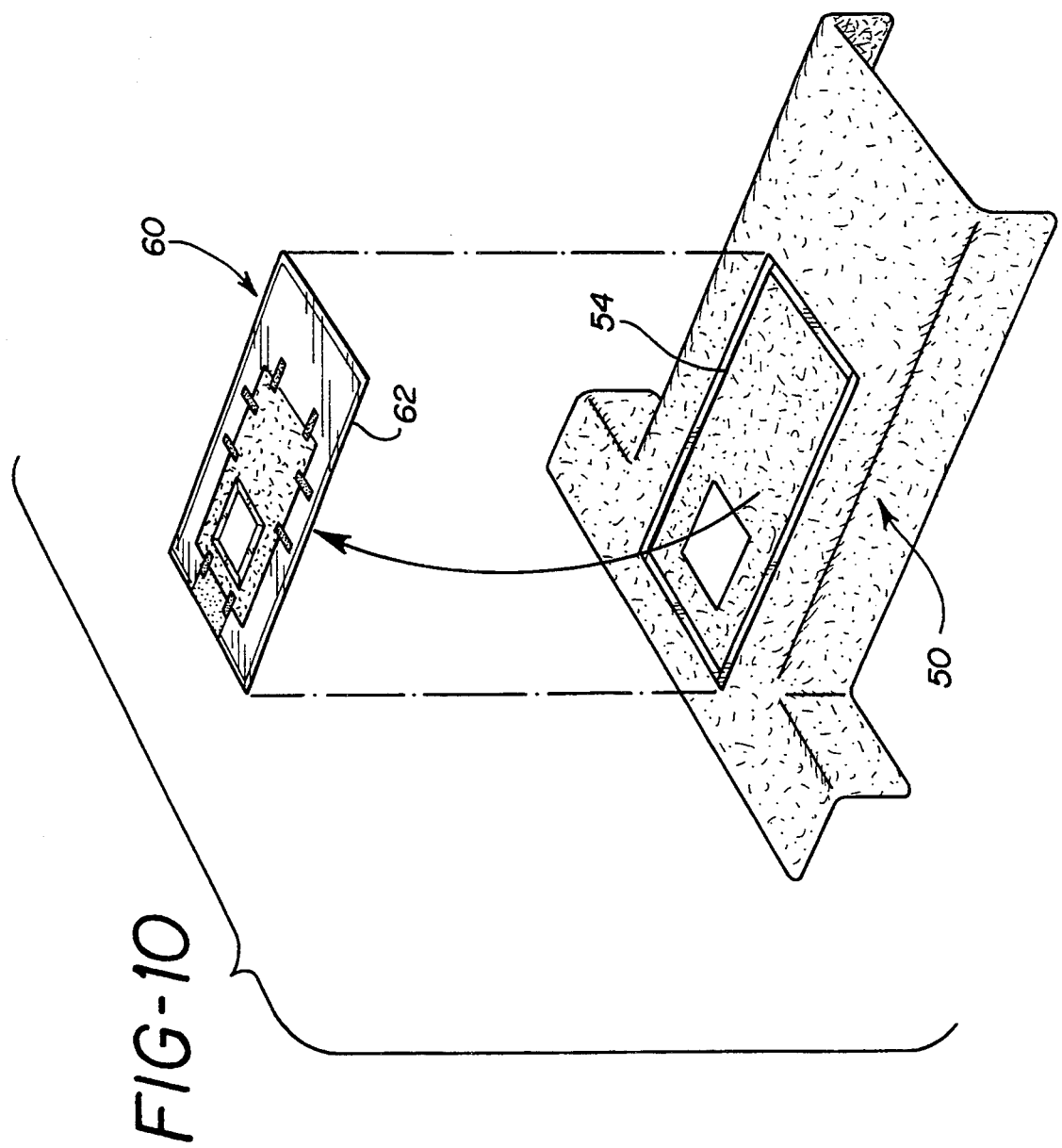
FIG. 10 is a perspective view of the drape of FIG. 9 after the surgical procedure has been completed and the top and bottom sheets of the drape have been separated.

FIG. 10 depicts the removal of top sheet 60 from bottom sheet 50 when the surgery is finished. Top sheet 60, including the elements that are attached to it, constitute red-bag contaminated waste. Bottom sheet 50 can be reused, recycled, or disposed of as uncontaminated brown-bag waste, depending on the material of sheet 50.

FIG. 10A depicts removal of top sheet 60A from bottom sheet 50A in an embodiment of this invention in which a velcro fastening system 54A and 62A is used to secure the top and bottom sheets together.

While this invention has been described in conjunction with certain specific embodiments thereof, it is evident that many alternatives, modifications, and variations will be apparent to those skilled in the art, in light of the above description. Accordingly, it is intended to embrace all such embodiments that fall within the spirit and broad scope of the appended claims.

We claim:

1. A multi-element surgical drape, comprising
   a) a bottom sheet for placement over a patient and comprising
      i) a bottom surface for contacting the patient,
      ii) a top surface for facing away from the patient after placement,
      iii) attachment receptor means on the top surface, and
      iv) a fenestration;
   b) a top sheet comprising
      i) a bottom surface facing the bottom sheet and a top surface facing away from the bottom sheet,
      ii) attachment means on the bottom surface that attach to the receptor means on the bottom sheet to removably secure the top sheet to the bottom sheet, and
      iii) a fenestration smaller than, and aligned with, the fenestration in the bottom sheet; and
   c) a pouch on the top surface of the top sheet, near the fenestration, for collecting fluid runoff during surgery, the pouch comprising
      i) a top edge and bottom edge joined by two opposing side edges, the side edges and bottom edge being sealed closed,
      ii) means for detachably sealing the top edge to permit opening the pouch to receive fluid and then closing the pouch to prevent leakage of the fluid.

2. The surgical drape of claim 1 in which the bottom sheet comprises a polyethylene nonwoven fabric.

3. The surgical drape of claim 1 in which the attachment means is a releasable adhesive and the attachment receptor means is a release layer that contacts the adhesive and facilitates separation of the sheets.

4. The surgical drape of claim 1 in which the attachment receptor means and attachment means in combination form a hook-and-loop fastener system.

5. The surgical drape of claim 1 in which the bottom sheet further comprises guide means to indicate a preselected position on the top surface and the top sheet is placed in the preselected position.

6. The surgical drape of claim 1 in which the top edge of the pouch has a flexible surface that may be pressed against a facing surface and the means for detachably sealing comprises a raised ridge on one surface for sealingly engaging a corresponding channel on the other surface.

7. The surgical drape of claim 1 in which the pouch further comprises a sealable drainage port through which fluid may be drained from the pouch.

* * * * *